United States Patent [19]

Burns et al.

[11] 4,049,381
[45] Sept. 20, 1977

[54] APPARATUS AND METHOD OF FLUID SAMPLE ANALYSIS

[75] Inventors: Donald A. Burns, Putnam Valley, N.Y.; Michael J. Brand, Bryan, Tex.; Alexander M. Saunders, Bedford Village, N.Y.

[73] Assignee: Technicon Instruments Corporation, Tarrytown, N.Y.

[21] Appl. No.: 669,785

[22] Filed: Mar. 23, 1976

[51] Int. Cl.² ............... G01N 31/00; G01N 33/16
[52] U.S. Cl. .......................... 23/230 R; 23/253 R; 23/230 B; 23/259
[58] Field of Search ........... 23/230 R, 230 B, 253 R, 23/259

[56] References Cited

U.S. PATENT DOCUMENTS

| | | | |
|---|---|---|---|
| 2,935,028 | 5/1960 | Ferrari, Jr. et al. | 23/253 R UX |
| 3,137,480 | 6/1964 | Isreeli | 23/253 R X |
| 3,334,969 | 8/1967 | Catravas | 23/253 R X |
| 3,432,271 | 3/1969 | Wasilewski | 23/253 R |
| 3,502,412 | 3/1970 | Burns | 356/40 |
| 3,505,021 | 4/1970 | Eveleigh | 23/230 R |
| 3,523,733 | 11/1970 | Kling et al. | 23/253 R X |
| 3,615,234 | 10/1971 | Ludvigsen | 23/253 R |
| 3,741,875 | 6/1973 | Ansley et al. | 23/230 B X |
| 3,816,075 | 6/1974 | Lambert | 23/230 R |
| 3,826,615 | 7/1974 | Smythe et al. | 23/230 R |

*Primary Examiner*—Joseph Scovronek
*Attorney, Agent, or Firm*—S. P. Tedesco; Stephen E. Rockwell

[57] ABSTRACT

Apparatus and method for obtaining a concentration gradient in a liquid sample analyzer including flowing a first liquid in a stream to fill a conduit, and continuing the flow of the first liquid along the conduit subsequent to the filling step. Combined with these steps is the step of changing the concentration of the first liquid by removing from the stream a predetermined varying volume of the first liquid and adding to the stream a predetermined proportional varying volume of a second liquid. There is also provided a method of serial dilutions of a liquid stream in a conduit by removal of a portion of the stream prior to each diluent addition for the purpose of conserving diluents which may be reagents.

10 Claims, 1 Drawing Figure

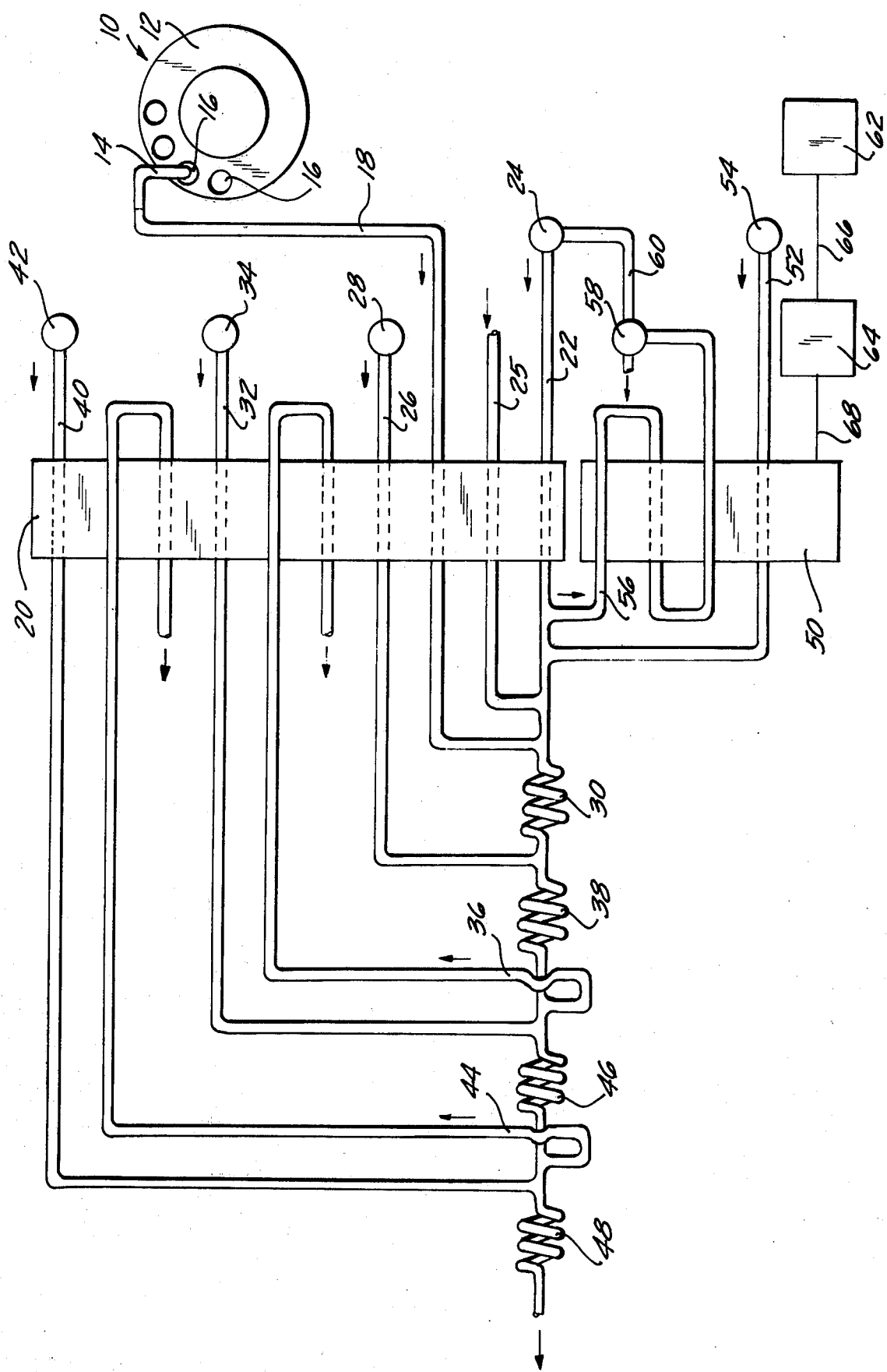

APPARATUS AND METHOD OF FLUID SAMPLE ANALYSIS

This invention relates to apparatus and method for diluting a liquid in sample analysis. Burns U.S. Pat. No. 3,502,412, Smythe et al U.S. Pat. No. 3,826,615 and Ansley et al U.S. Pat. No. 3,741,875 are typical of the known prior art. Burns discloses a method for automatically determining the osmotic fragility of red blood cells by continually admixing a stream of red blood cells with a stream of saline solution gradient of continually changing salt concentration to produce a suspension of the cells in the gradient and then measuring the light transmission through the suspension to determine the osmotic fragility. At the same time that red blood cells are being added to the stream of saline solution issuing from a mixing vessel, the salt concentration of the saline solution in the mixing vessel is continually being decreased by withdrawing solution while simultaneously adding water. By varying the rate of saline solution withdrawal in comparison to water addition, a preselected salt gradient may be maintained.

Smythe et al disclose flowing a gas-segmented liquid stream along a conduit. During such flow, all the gas segments of the stream are removed and downstream gas segments are added to the stream. This removal and addition utilizes a single pump which, when operated, is run at a constant speed. The pump is not operated continuously. Ansley et al disclose in FIG. 2 the serial addition to a liquid stream of plural diluents or reagents in sample analysis.

An object of the invention is to provide an improved apparatus and method for diluting a liquid in liquid sample analysis. A further object of the invention resides in the conservation of one or more diluents or reagents. Still other objects of the invention will be apparent from the following detailed description of the preferred embodiments.

In the drawing there is illustrated schematically apparatus embodying the invention.

In the drawing, there is indicated generally at 10 a conventional sample supply in the form of an angularly movable tray 12 and movable relatively to an off-take tube 14 for the sequential off-take of liquid samples 16 in circular array on the tray 12. The off-take tube is coupled to a compressible pump tube 18 extending through a first peristaltic pump 20, the outlet of the tube 18 being coupled to a first conduit or compressible pump tube 22 extending through the pump and having the inlet end thereof coupled to a liquid source 24 such as a vessel of a first liquid. A compressible pump tube 25 extends through the pump 20, having an open inlet end exposed to the ambient atmosphere, the outlet end thereof being coupled to the conduit 22 as shown. A similar tube 26 extends through the pump 20, having an inlet end coupled to a liquid source 28. The other end of the tube 26 is coupled to the first conduit 22. A mixing coil 30 is interposed in the conduit 22 as shown. A similar tube 32 extends through the pump 20, having an inlet end coupled to a liquid source 34. The outlet of tube 32 is coupled to the conduit 22 as shown. Upstream of the last-mentioned coupling, a similar tube 36 has an inlet and coupled to the conduit 22. The tube 36 extends through the pump 20 and has an outlet directed to waste. A mixing coil 38 is interposed in the conduit 22 as shown.

Extending through the pump 20 is a similar tube 40 having an inlet end coupled to liquid source 42 and having an outlet coupled to the conduit 22 as shown. A similar tube 44 has an inlet end coupled to the conduit 22 as shown, the tube 44 extending through the pump and having an outlet directed to waste. The conduit 22 has a mixing coil 46 interposed therein as shown. A mixing coil 48 is interposed in the conduit 22 as shown, which conduit 22 is directed to a nonillustrated flow-through cell for red blood cell examination in this example. The liquid sources 24, 28, 34 and 42 may be of reagents and/or diluents and in the form illustrated by way of example only, are a 9% solution of NaCl, red blood cells in suspension, a 9% solution of NaCl and a 9% solution of NaCl, respectively. The samples 16 are different samples of saponin. The aforementioned nonillustrated flow cell may be utilized for the determination of red blood cell osmotic fragility testing by counting cells in a conventional manner.

The pump 20 is operated at constant speed for the sequential flow therethrough of the samples 16 along the pump tube 18 to the first conduit 22, and a wash solution may be supplied to the off-take tube 14 between samples in a nonillustrated manner utilizing the apparatus disclosed in Gordon et al U.S. patent application Ser. No. 537,615 now U.S. Pat. No. 3,960,020 issued June 1, 1976. The liquid flowed from the source 24 by the pump 20 through the conduit 22 is segmented in the latter by air flowing in a similar manner through tube 25, and the liquid 16 samples are superimposed in sequential manner on such segmented stream. Prior to the addition to the stream of the diluent from the source 34 flowing through the tube 32, a mixture of liquid from the stream in the conduit 22 is removed by the conduit 36 without significant removal of any undissolved air therein through the utilization of the fitting of Hrdina U.S. Pat. No. 3,640,822 in the coupling of the tube 36 to the conduit 22. Such a fitting is also utilized in the coupling of the inlet of the tube 44 to the conduit 22. The flow rates in the tubes 36 and 44 are the same as the flow rates of the tubes 32 and 40, respectively. The off-take through the tubes 36 and 44 substantially reduces and conserves the volumes of the respective diluents which are added through the tubes 32 and 40, and facilitates mixing of each of the last-mentioned diluents in the coils 46 and 48, respectively. As previously indicated, these diluents may be reagents in other uses of the apparatus and method, and such conservation of such liquids may substantially reduce reagent costs in analysis.

The portion of the apparatus for the preparation of a liquid concentration gradient involves a second peristaltic pump 50. The pump 50 has two channels through one of which extends a compressible pump tube 52 having an inlet end coupled to a diluent source 54 which may be water. The outlet end of tube 52 is coupled to the conduit 22. A similar tube 56 has an inlet end coupled to the conduit 22 as shown. The tube 56 is directed through the pump 50 and has an outlet end coupled to the intake of a three-way valve 58 operative in one position thereof to return the off-take portion of the flow through the tube 56 to the source 24 through a conduit 60 to conserve the diluent, the other position of the valve 58 being that directing the outflow from the tube 56 to waste as shown.

The pump 50 has a variable speed motor which is controlled through a programmer by a function generator, oscillator or clock, a function generator being indicated by way of example at 62 and having an output to the programmer 64 through a cable 66. The programmer 64 has an output to the variable speed motor through a cable 68.

The operation of the gradient preparation apparatus and the method thereof when the output from valve 58 is coupled by the conduit 60 to the source 24 is as follows. There is no preparation of a concentration gradient when the pump 50 is off. When the programmer 64 receives a signal from the function generator 62 and energizes and increases the speed of the motor of the pump 50 through a signal supplied along line 68 thereto, the speed of the pump 50 may increase up to a speed which may be somewhat below or equal to but not above the speed of the pump 20. The operation of the variable speed motor pump 50 may be linear or non-linear. For example, the operation of the pump 50 may be such as to increase the off-take of the liquid of the source 24 from the conduit 22 through the pump tube 56 for return of the source 24 in a linear manner, with diluent of the source 54 being added to the stream in the conduit 22 through the tube 52 also in linear manner. In the preferred form, the flow rates in the tubes 52 and 56 are the same. Use of the pulse generator 62 enables the gradient curve to assume any desired shape. For example, the concentration gradient may be increased during the run of a single sample or a series of samples and then reduced during the running of such samples or series of samples. Further, the speed of the pump 50 may be increased continually over a period of time, then operated continually over a period of time at constant speed, and then decreased continually over a period of time, for example. It will be obvious that if the liquids of the respective sources 24 and 54 are switched, the gradient produced by the operation of the pump 50 during the running of a single sample or a series of samples is decreased rather than increased initially. The gradient preparation method and the apparatus for performing the same has the advantage, among others which are obvious, that it does not require a mixing vessel and has the further advantage that the gradient is prepared very quickly.

While plural forms of the preferred method and apparatus have been illustrated and described, it will be apparent, especially to those versed in the art, that the invention may take other forms and is susceptible to various changes in details without departing from the principles of the invention.

What is claimed is:

1. A method of preparing a concentration gradient, comprising the steps of: flowing a first liquid from a source in a stream along a first conduit to fill said conduit; continuing said flow of said first liquid along said first conduit subsequent to said filling step; and removing a portion of said first liquid from said stream through a second conduit coupled to said first conduit and at a controlled varying rate and concurrently adding a second liquid to said stream through a third conduit coupled to said first conduit and at a controlled varying rate, the junction of said third and first conduits being downstream from the junction of said second and first conduits, said rates of removal from and addition to said stream in said first conduit being the same.

2. A method as defined in claim 1, further including returning to said source said portion of said first liquid removed from said stream.

3. A method as defined in claim 1, further including varying said rates of removal from and addition to said stream linearly.

4. A method as defined in claim 1, further including varying said rates of removal from and addition to said stream non-linearly.

5. A method as defined in claim 1, further including increasing said rates of removal from and addition to said stream over a given time period.

6. A method as defined in claim 5, further including subsequently decreasing said rates of removal from and addition to said stream following said given time period.

7. A method as defined in claim 1, further including flowing a volume of a third liquid into said first conduit in a fourth conduit coupled to said first conduit downstream from the junction of said first and third conduits, and removing from said first conduit through a fifth conduit coupled to said first conduit a volume of said stream, the junction of said fifth and first conduits being intermediate the junctions of said fourth and first conduits and said third and first conduits.

8. A method as defined in claim 1, further including segmenting said first liquid with segments of an immiscible fluid.

9. Apparatus for preparing a concentration gradient, comprising: means for flowing a first liquid from a source along a first conduit, first flow means for removing a portion of said first liquid from said first conduit through a second conduit coupled to said first conduit, second flow means for adding a second liquid to said first conduit along a third conduit coupled to said first conduit, the junction of said third and first conduits being downstream from the junction of said second and first conduits, and means for operating said first and second flow means at a same flow rate, so as to provide a concentration gradient of said second liquid along said first conduit, said operating means including further means for concurrently varying the respective flow rates of said first and second flow means.

10. Apparatus as defined in claim 9, further including means for directing the outflow of said second conduit to said source.

* * * * *